(12) United States Patent
Muellinger et al.

(10) Patent No.: US 7,866,317 B2
(45) Date of Patent: Jan. 11, 2011

(54) INHALATION DEVICE

(75) Inventors: Bernhard Muellinger, Munich (DE); Andreas Wenker, Landsberg am Lech (DE); Dorothee Koerber, Augsburg (DE); Gerhard Scheuch, Wohratal (DE)

(73) Assignee: Activaero GmbH (DE)

( * ) Notice: Subject to any disclaimer, the term of this patent is extended or adjusted under 35 U.S.C. 154(b) by 874 days.

(21) Appl. No.: 11/367,618

(22) Filed: Mar. 3, 2006

(65) Prior Publication Data

US 2006/0201499 A1   Sep. 14, 2006

(30) Foreign Application Priority Data

Mar. 8, 2005   (EP)   ................... 05005033

(51) Int. Cl.
  *A61M 11/00*   (2006.01)
(52) U.S. Cl. .............................. 128/204.18; 128/204.21
(58) Field of Classification Search ............ 128/204.18, 128/204.21, 204.23
  See application file for complete search history.

(56) References Cited

U.S. PATENT DOCUMENTS

| | | | |
|---|---|---|---|
| 5,303,698 A * | 4/1994 | Tobia et al. ............ | 128/204.21 |
| 6,644,310 B1 | 11/2003 | Delache et al. | |
| 2001/0054421 A1 | 12/2001 | Jaser et al. | |
| 2004/0065321 A1 * | 4/2004 | Stenzler ................. | 128/200.14 |
| 2005/0031322 A1 * | 2/2005 | Boyle et al. ................. | 388/800 |
| 2005/0034724 A1 * | 2/2005 | O'Dea .................... | 128/204.18 |
| 2005/0155602 A1 * | 7/2005 | Lipp ..................... | 128/203.12 |

FOREIGN PATENT DOCUMENTS

| | | |
|---|---|---|
| DE | 199 39 417 C2 | 3/2001 |
| DE | 100 22 795 B4 | 11/2001 |
| EP | 1 258 264 A2 | 11/2002 |
| EP | 1 491 227 A2 | 12/2004 |
| WO | WO 98/52633 A | 11/1998 |
| WO | WO 00/58022 A | 10/2000 |

OTHER PUBLICATIONS

European Search Report, dated Sep. 16, 2005 (6 pages).

* cited by examiner

*Primary Examiner*—Steven O Douglas
(74) *Attorney, Agent, or Firm*—Faegre & Benson LLP

(57) ABSTRACT

An inhalation device may include a control and an air pump that is connected to the control. The air pump is controlled by the control such that the air pump supplies an inhalation flow, or inhalation volume or both according to a predetermined time course to a nebulizer connected to the air pump. The inhalation flow, inhalation volume or both is controlled by controlling the air pump, rather than by using valves.

30 Claims, 4 Drawing Sheets

INHALATION DEVICE

Figure 1:
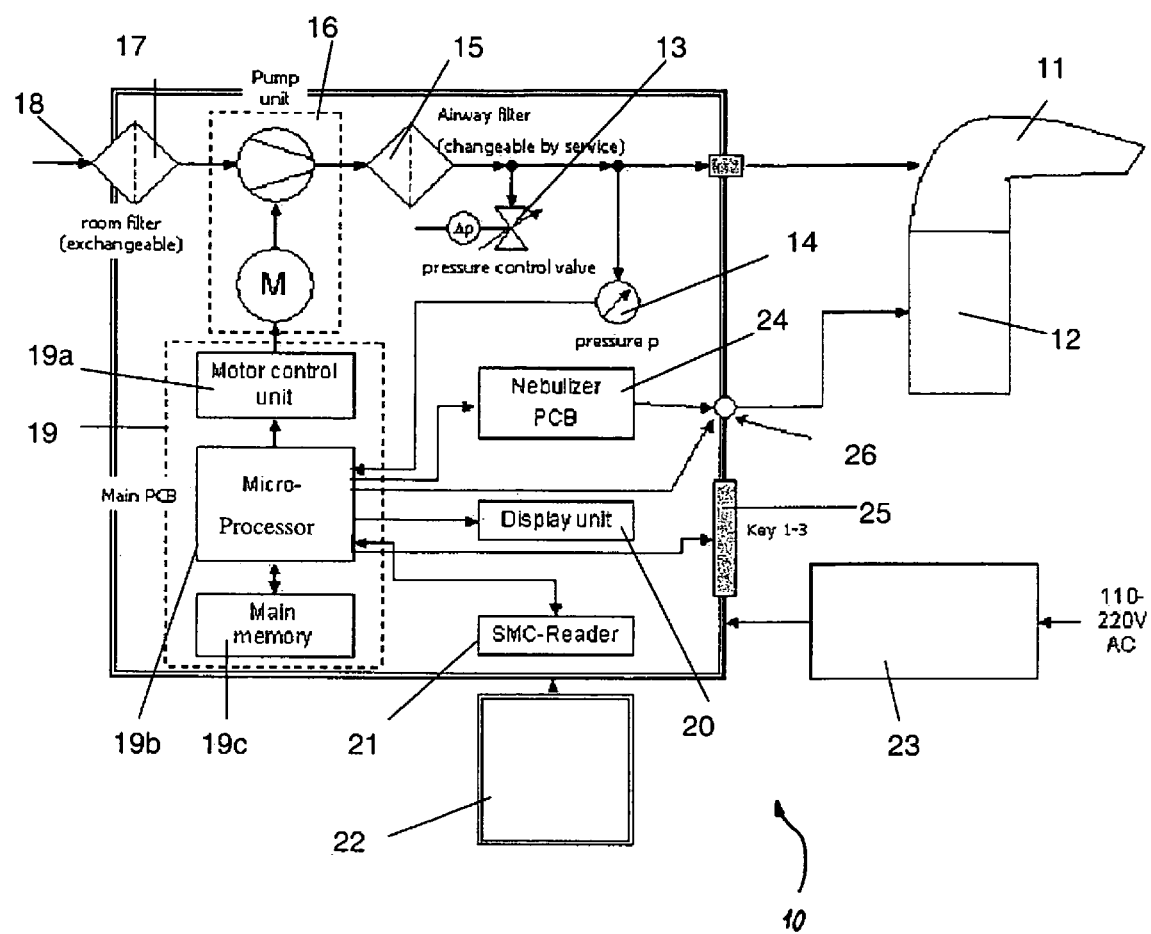
Figure 2:
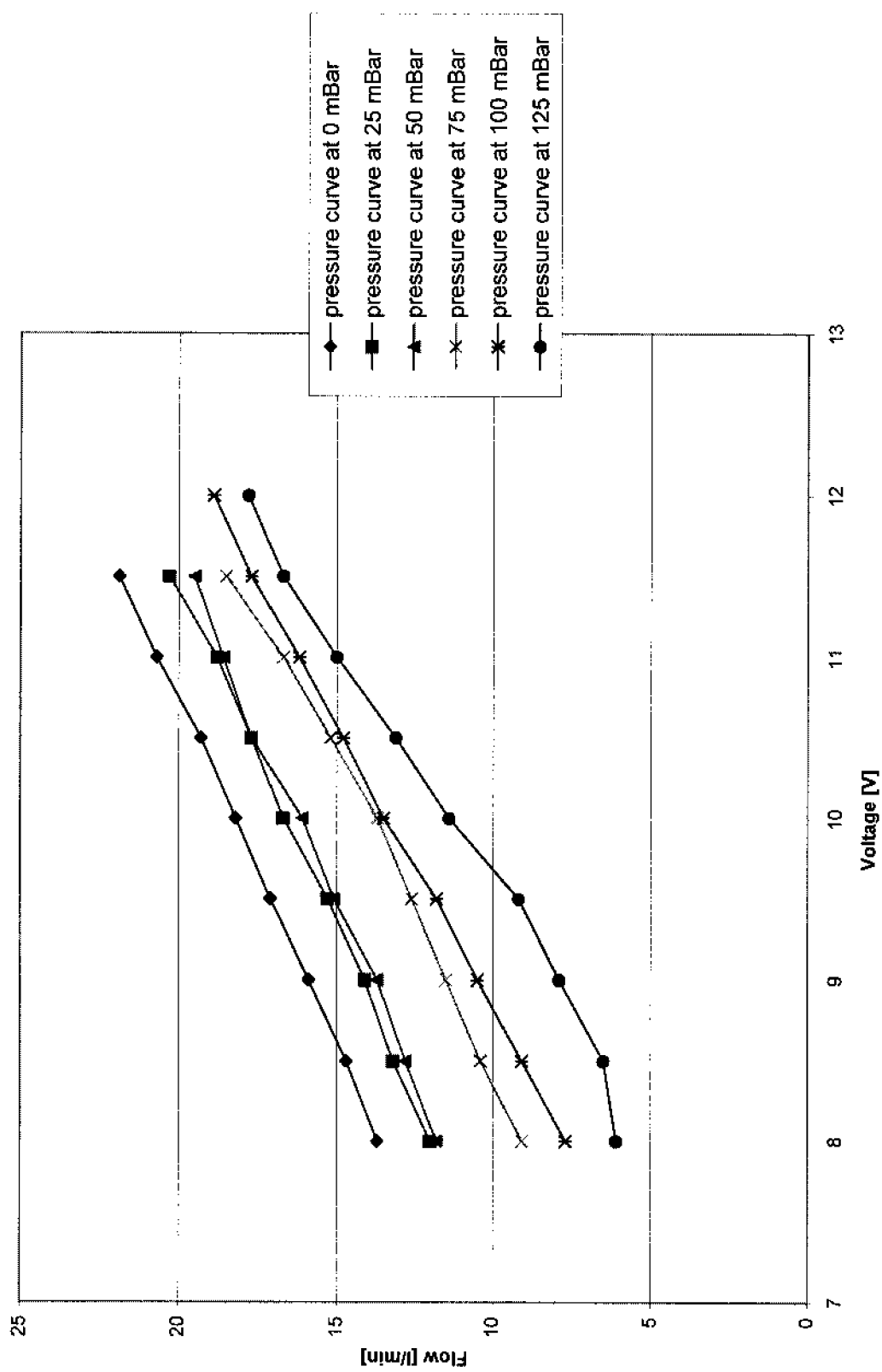
Figure 3:
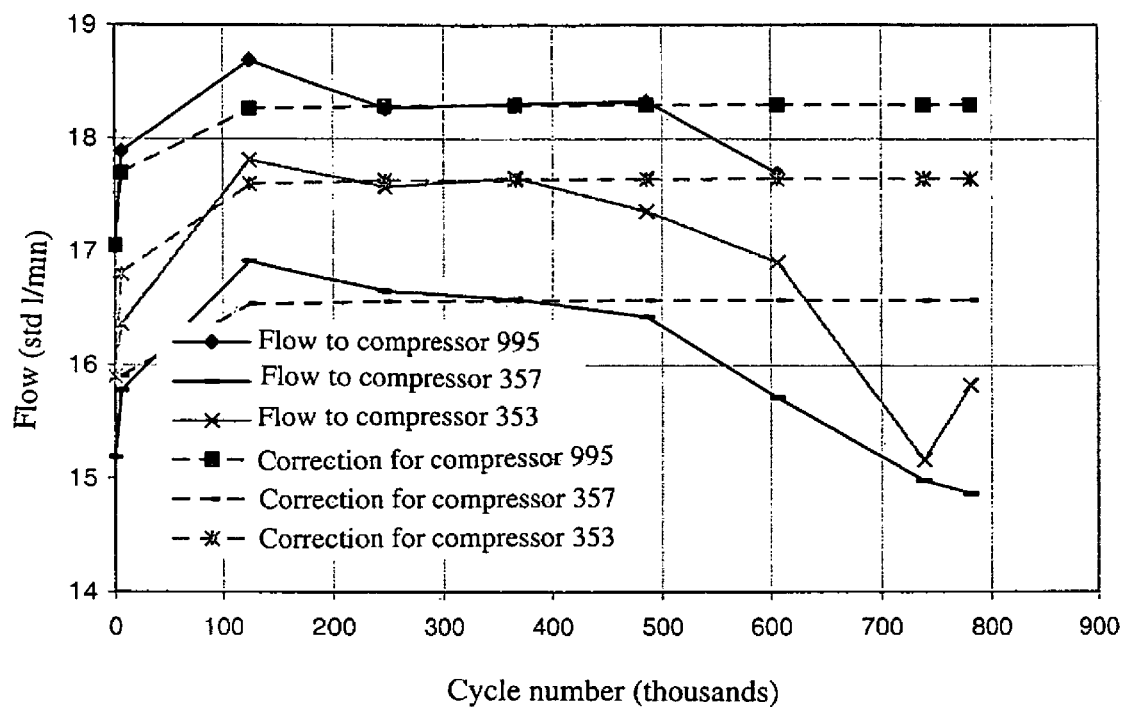

This application claims priority to EP application 05005033.5 filed Mar. 8, 2005.

FIELD OF THE INVENTION

The invention relates to a device for the application of a pharmaceutical via the lung.

BACKGROUND

Inhalation is a way which is getting more and more important for the administration of pharmaceuticals. To this end, apart from the use of new locally acting pharmaceuticals for the therapy of lung diseases, new therapeutic strategies are developed making use of the lung as a site for systematically acting substances.

Regarding the application of drugs via inhalation, the demands on the quality of the inhalation process are increasing. The pharmaceutical dosage prescribed by the medical practitioner must be applied as exactly and reproducible as possible, wherein the administered dosage and its reproducibility depend basically on the breathing processes.

In everyday life in hospitals, the breathing maneuvers or processes by a patient cannot be influenced very much and evades medical control so that an exact guideline for respiratory volume and breath flow upon inhalation of therapeutic aerosols is desirable. This would lead to a significant improvement in the inhalation therapy and its reproducibility.

The administration of pharmaceuticals in the form of aerosol to the lung by inhalation is essentially influenced by four factors: (i) the particle size and particle properties of the aerosol; (ii) the volume inhaled by the patient in one breath; (iii) the patient's respiratory flow; and (iv) the patient's morphometry and respiratory system. Although aerosols in suitable particle size ranges are produced by the conventional systems, the parameters "respiratory volume" and "respiratory flow" (rate of breathing) are taken into account either insufficiently or not at all in known systems. This leads to an uncontrolled inhalation of the aerosol, which in turn has the result that the aerosol particles reach the lung in insufficient amounts or do not reach the areas (e.g., the alveolar area) within the lung to be treated.

WO 98/52633 discloses a device for administering a pharmaceutical via the lung comprising a mouthpiece for inhalation to which an adjustable atomizer is assigned, and a compressed air control valve through which a predefinable volume flow of compressed air can be delivered for a predefinable period to the atomizer containing the liquid medicine. Such a compressed air control valve is indispensable in the known inhalation device since high pressures are necessary to atomize the drug.

SUMMARY OF THE INVENTION

It is the object of the invention to provide a functionally simply designed device. This object is achieved by an inhalation device comprising a control; and air pump connected to the control, wherein the control controls the air pump such that it supplies an inhalation flow, or an inhalation volume or both according to a predetermined time course to a nebulizer connected to the air pump as recited in claim 1. Preferred features, which form advantageous embodiments of the invention, are covered by the dependent claims.

The invention starts from the basic idea that a desired or predetermined inhalation volume or a desired or predetermined inhalation flow is provided by a corresponding control of the air pump. This is advantageous in that no valves, except for a pressure relief valve as safety valve, are necessary to curb or control the inhalation volume/inhalation flow. Regulating valves are compulsory in known inhalation devices in order to be able to handle the high pressures necessary for the nebulization of the pharmaceutical.

A control is provided to control the air pump in the inhalation device according to the invention, which controls the air pump such that it supplies an inhalation flow and/or an inhalation volume according to a predetermined time course to a nebulizer attached to the air pump. The nebulizer preferably comprises a mouthpiece or a tube piece via which the patient inhales.

The inhalation flow and/or the inhalation volume is preferably basically constant during the predetermined time course. Alternatively, the inhalation flow and/or the inhalation volume differs in level during the predetermined time course. Preferably, the inhalation flow and/or the inhalation volume is basically kept constant at the respective level.

The predetermined inhalation flow and the predetermined inhalation volume are preferably an inhalation flow and an inhalation volume, respectively, with which an optimum inhalation and treatment of the patient are achieved, depending on the individual patient parameters and/or aerosol parameters for an individual treatment of an individual patient, said parameters being determined for this patient prior to the inhalation. Optimum inhalation means a specific individual deposit of the individual active ingredient dosage to be administered into the lung or specifically selected areas of the lung, i.e., the specific deposit of a predetermined active ingredient amount in a predetermined area of the lung. The individualisation takes place in this respect depending on the individual patient and/or aerosol parameters, i.e., depending on at least one of said parameters, it is predetermined which active ingredient dosage is necessary for the treatment upon deposit in the desired area of the lung.

Preferably, the air pump is controlled via the control by the voltage or pulse-width modulation of a square wave signal with constant or variable voltage. This means that the control voltage of the air pump is predetermined or controlled such by the control that the air pump generates the desired or predetermined inhalation flow and/or the desired or predetermined inhalation volume. According to the invention, the desired inhalation flow and/or the desired inhalation volume are set via a direct control of the air pump (and not like in conventional systems via additional regulating valves). Preferably, this takes place depending on patient-individual lung function parameters, as described above. Said patient-individual lung function parameters are preferably inhalation flow and/ or inhalation volume of the individual patient, i.e., the lung volume of the patient (if necessary with a safety reduction) and the inhalation flow achievable by the patient or regarded as comfortable. According to a preferred embodiment of the invention, the patient data which are derived or calculated from said patient-individual lung function parameters and which correspond to these lung function parameters are stored on a storage medium, which is readable by the inhalation device with an appropriate reader. Said data are stored on the storage medium, e.g., by the treating practitioner or the institution in charge. The storage medium is either an internal storage medium, i.e., a storage medium of the inhalation device, which is accessible (e.g., via key entries or data lines and modems), or a separate, external storage medium. The data carrier is, e.g., a SmartCard device, and the reader is a SmartCard device reader. The patient-individual lung function parameters and/or the corresponding patient data are stored on the SmartCard device, e.g., by the treating practitioner. The SmartCard device contains all individual data necessary for the inhalation so that the patient can also inhale, for example, at home, the necessary pharmaceutical with the inhalation device according to the invention. This means that the surveillance of the treating practitioner is not necessary.

The control calculates corresponding control parameters on the basis of the patient-individual data stored on the storage medium. The pump voltage is derived from said control parameters that are used to obtain the necessary inhalation flow.

Preferably, the characteristic of the air pumps used are at first individually metrologically determined and subsequently mathematically approximated for each inhalation device. Said mathematical approximation is then stored in the control for the operation of the inhalation device to carry out the correction. This is preferably done according to the invention with the following equation:

$$U = x \frac{V}{1/\min} (Q_{target} - Q_{measurement}) + U(Q_{measurement}) - yV \cdot e^{\frac{z}{cycle\,number}}$$

wherein:
$Q_{target}$: desired flow in 1/min
$Q_{measurement}$: measured flow in 1/min (at the beginning) at the voltage $U(Q_{measurement})$
x, y, z: constants determined by measurements Preferred values for the parameters x and y are in the ranges of $0.3 < x < 0.9$ and $0.6 < y < 1.2$, respectively. More preferably, $x = 0.59$ and $y = 0.89$. Preferred values for z are in the range from $3,000 < z < 5,000$. More preferably, $z = 4,000$.

In the above indicated preferred formula for the evaluation of the control voltage, the course of the flow is considered depending on the cycle number for an individually used air pump. Said characteristic flow vs. cycle number varies from air pump to air pump and further the flow provided by an air pump is not constant over the cycle number.

In order to control the inhalation flow or the inhalation volume during inhalation, preferably a pressure sensor is provided. Using the signal provided by this pressure sensor, the control can compare the actual inhalation flow (actual flow) with the predetermined inhalation flow (target flow) and then, if necessary, vary or control the control voltage of the air pump in order to remove deviations of the actual inhalation flow from the predetermined inhalation flow. Preferably, this is done according to the invention by means of the following formula:

$$\Delta p = xQ^2 + yQ$$

wherein:
$\Delta p$: pressure difference
Q: flow
x, y: constants determined by measurements The pressure sensor is preferably also used for the detection of errors. If the pressure measured by the pressure sensor differs from the pressure of the pump, it may be an indication, e.g., of a clogged filter which has to be changed.

Moreover, it is preferred that the control considers the counter-pressure produced consciously or unconsciously by the patient during inhalation. This takes place, e.g., via corresponding characteristics stored in the control. An inhalation flow is generated by the air pump for a certain control voltage of the air pump depending on the counter-pressure of the patient. If the counter-pressure of the patient rises, the inhalation flow decreases for said certain voltage. Accordingly, the inhalation flow increases for a fixed voltage if the counter-pressure decreases. In order to offset such deviations and influences by the patient, the control voltage of the air pump is varied and controlled depending on the counter-pressure of the patient such that the flow remains essentially constant.

The control of the inhalation device according to the invention preferably comprises a control, i.e., a motor-control for the drive of the air pump, a processing unit in the form of a microprocessor as well as a memory (working memory). Furthermore, the inhalation device preferably comprises a display unit and an input unit.

The safety valve already mentioned as well as the pressure sensor already mentioned are arranged downstream from the air pump in arbitrary order.

The air pump of the inhalation device is preferably a compressor or a turbine.

A further aspect of the present invention relates to the control of the inhalation process. According to this aspect of the present invention, the patient has the possibility to choose the pharmaceutical to be inhaled if the patient is treated with several pharmaceuticals. Further, the patient has the possibility to individually modify the inhalation volume and deviate from the predetermined inhalation flow, e.g., depending on his respective "form on the day". As soon as the patient starts to inhale and the pressure sensor realizes this (a suction of the patient at the mouthpiece or nebulizing tube is recognised as start of the inhalation by the pressure sensor), the control considers the choice of the patient made directly before as fixed. If the inhalation is successfully terminated, the patient's predetermined, i.e., modified parameters remain stored in the control and the next inhalation process starts on the basis of the "old" inhalation volume or inhalation flow, chosen prior to the preceding inhalation and the pharmaceutical chosen prior to the preceding inhalation, as long as the patient does not perform a resetting. However, if the inhalation process is terminated by the patient since, e.g., the chosen or modified inhalation volume is not agreeable for the patient, the control asks whether the inhalation started should be continued or terminated. In the latter case the control demands that the patient reset the parameters.

According to the invention, the recognition of the start of the inhalation process takes place via the pressure sensor. As soon as the control recognises the start of an inhalation device, the air pump is activated. In other words, according to the invention, the air pump is not constantly in operation but only during the inhalation process, i.e., the inspiration process, but not during the breaks and expiration processes.

Thus, the device according to the invention provides the patient with simple means to inhale an exactly predetermined pharmacon volume with exactly predetermined respiratory flow. In a way, the patient is given artificial respiration since the inhalation device sets and adjusts the respiratory flow. To this end, the separate air supply already provided for therapeutical nebulizers in clinical everyday life is advantageously controlled such that only a predetermined air volume is delivered to the nebulizer with a predetermined flow. According to the invention, the air of the nebulizer is set to a pre-selectable volume flow rate, which cannot be influenced by the patient, thus resulting in a constant flow. The additional air volume flow is then preferably started by an electronic control over a predetermined time course in order to thus apply an exactly predetermined air volume.

According to a preferred embodiment, a regulator for keeping the volume flow constant is arranged before the adjustable nebulizer, wherein a pressure gauge is preferably arranged after the regulator to control a predetermined volume flow.

It is furthermore advantageous for the practical use of the device that a pressure gauge is provided which is preferably responsive to suction pressure in the inhalation mouthpiece in order to trigger the nebulization start of the nebulizer.

According to the invention, it is an advantage that a wide range of breathing manoeuvres can be developed in the medical treatment by the simultaneous choice of inhalation flow and inhaled volume, wherein the place of deposit in the lung can be influenced as desired via various breathing manoeuvres. Thus, it is possible to deposit pharmaceuticals which should be acting in central lung areas, for instance, predominantly there.

A further advantage of the device according to the invention is that thus inhalations of patients as a matter of routine in the clinical field can be improved because a patient does not have any problems regarding the synchronisation of the start of the nebulization of the pharmaceuticals and the start of the inhalation due to the provided breath triggering of the inhalation. Moreover, it is an advantage that errors during the inhalation which are due to an improper handling of the nebulizer can be considerably reduced.

BRIEF DESCRIPTION OF THE DRAWINGS

The invention is hereinafter explained in further detail with the drawings. They show:

FIG. 1 a schematic depiction of an embodiment of a device according to the invention;

FIG. 2 a depiction of the flow depending on the voltage of the pump and the counter-pressure of the patient;

FIG. 3 the change in the flow provided by the pump depending on the cycle number; and FIG. 4 a preferred arrangement of the air pump in the inhalation device.

DETAILED DESCRIPTION

FIG. 1 schematically shows the interaction of individual components of an inhalation device 10 according to the invention. The device 10 for the application of a pharmaceutical aerosol via the lung comprises an inhalation mouthpiece 11 with an associated nebulizer 12. A safety valve 13, a pressure sensor 14, an exchangeable filter 15 (or pressure attenuator), a (pressure) air pump 16, a further exchangeable filter 17, and an air inlet 18 are operably connected to the inhalation mouthpiece 11. The filter 17 is assigned to the air inlet 18 in order to filter the air supplied to the air pump 16. The filter 15, the pressure sensor 14 and the safety valve 13 are arranged downstream from the air pump 16. The pressure sensor 14 is responsive to suction pressure in the mouthpiece 11 to trigger the nebulization start of the nebulizer 12.

An electronic control 19 comprising a motor control 19*a*, a microprocessor 19*b* and a memory 19*c*, is functionally connected to the pump 16, the pressure sensor 14 and to the nebulizer 12 via corresponding nebulizer electronics 24 (printed circuit board PCB). The nebulizer electronics are preferably simply exchangeable so that the corresponding electronics can be used for the respective nebulizers. The nebulizer is connectable to the inhalation device via a connecting point 26. Preferably, the connection 26 is an encoded connection, which thus enables an automatic recognition of the connected nebulizer. Thus, a plausibility test can be carried out, e.g., whether the pharmaceutical to be administered can be applied with the connected nebulizer at all.

Further an optical display unit 20 is provided in order to show the patient the current inhalation flow. The display also serves to display the name of the pharmaceutical currently used, error messages, etc. The display preferably also serves to display the error messages of the nebulizer. Thus, upon use of a liquid nebulizer, a demand to refill, stop or a malfunctioning can be displayed in case there is no liquid in the nebulizer anymore.

The pressure sensor 14 serves to keep the inhalation flow constant in a value range from, e.g., 0-1,000 $cm^3/s$.

In the electronic control 19, the pharmaceutical and the inhalation volume are further adjustable via an input unit 25, e.g., via a keyboard or individual input keys.

Further, the inhalation device according to the invention comprises a SmartCard device reader 21 via which individual inhalation parameters such as inhalation flow and inhalation volume stored on a SmartCard device 22 can be read in. Alternatively, the individual parameters are stored in the memory 19*c*.

A power supply unit 23 (e.g., 110-240 V) supplies the inhalation device 10 with current.

The inhalation is carried out such that the patient sucks at the mouthpiece 11, whereby the pressure sensor 14 reacts and automatically starts the inhalation. The nebulizer 12 is supplied with compressed air via the pump 16 during the inhalation, and the desired pharmaceutical in the form of aerosol emits with the pre-selected or predetermined flow from the mouthpiece 11. After expiry of the inhalation period and/or achievement of the inhalation volume, the air supply is interrupted and the patient cannot inhale any further. This means that according to the invention, the control only controls or activates the air pump when the start of an inhalation process is recognised by the pressure sensor 14. When the inhalation process is terminated, the air pump 16 is deactivated again by the control 19.

A further aspect of the present invention is described by referring to FIG. 2. FIG. 2 shows different flow-voltage characteristics for various counter-pressures generated by the patient during inhalation. Basically, FIG. 2 shows that the flow provided increases when the voltage increases, i.e., the control voltage of the pump 16. For a certain voltage, e.g., 10.0 V, the flow provided by the pump decreases the more the counter-pressure of the patient increases. In FIG. 2, the uppermost characteristic corresponds to a counter-pressure of 0 mbar while the lowest characteristic corresponds to a counter-pressure of 125 mbars. The curves in-between correspond to pressures of 25, 50, 75 and 100 mbars. This means that the pump voltage has to be varied accordingly to correct the inhalation flow upon varying counter-pressure. If, e.g., the counter-pressure generated by the patient increases, the flow decreases at a predetermined voltage. The voltage has to be increased in order to again provide the necessary inhalation flow on the characteristic for this counter-pressure. The same is vice-versa true for a decrease in the counter-pressure generated by the patient. According to the invention, said characteristics are stored in the control so that the control can correspondingly control the pump depending on the counter-pressure generated by the patient and reset the voltage.

FIG. 3 shows a further preferred correction possibility of the inhalation device according to the invention. FIG. 3 shows flow-cycle-number characteristics of three air pumps identical in construction. The characteristics correspond to the solid lines, whereas the dashed lines in FIG. 3 correspond to corrected characteristics. FIG. 3 clearly shows that the flow provided by a certain pump increases to a maximum during the first 100 to about 120,000 cycles, and then, however, decreases gradually again. In particular, after 500,000 inhalation cycles, a greater decrease is noticeable. The flow-voltage characteristic is measured at first for an air pump used in an inhalation device according to the invention since the flow values of the compressors differ from each other. Subsequently, the flow values are mathematically approximated on the basis of the flow-cycle-number characteristics so that a simple correction possibility for the control is provided.

The following table shows how different the various flow-cycle-number characteristics can be:

| Cycle number | Flow average (l/min) Pump 1 (0338000995) | Flow average (l/min) Pump 2 (0412000357) | Flow average (l/min) Pump 3 (0412000353) | Deviation from initial value 1 (l/min) | Deviation from initial value 2 (l/min) | Deviation from initial value 3 (l/min) |
|---|---|---|---|---|---|---|
| 486,000 | 18.33 | 16.43 | 17.35 | 1.29 | 1.24 | 1.45 |
| 606,000 | 17.70 | 15.72 | 16.91 | 0.65 | 0.53 | 1.01 |
| 738,500 | off | 14.98 | 15.17 | off | −0.20 | −0.74 |
| 781,000 | off | 14.86 | 15.83 | off | −0.32 | −0.07 |

The pump voltage of 11 V was used for these measurements. During one cycle, the pumps were on for 5 s and off for 5 s.

Figure 4:
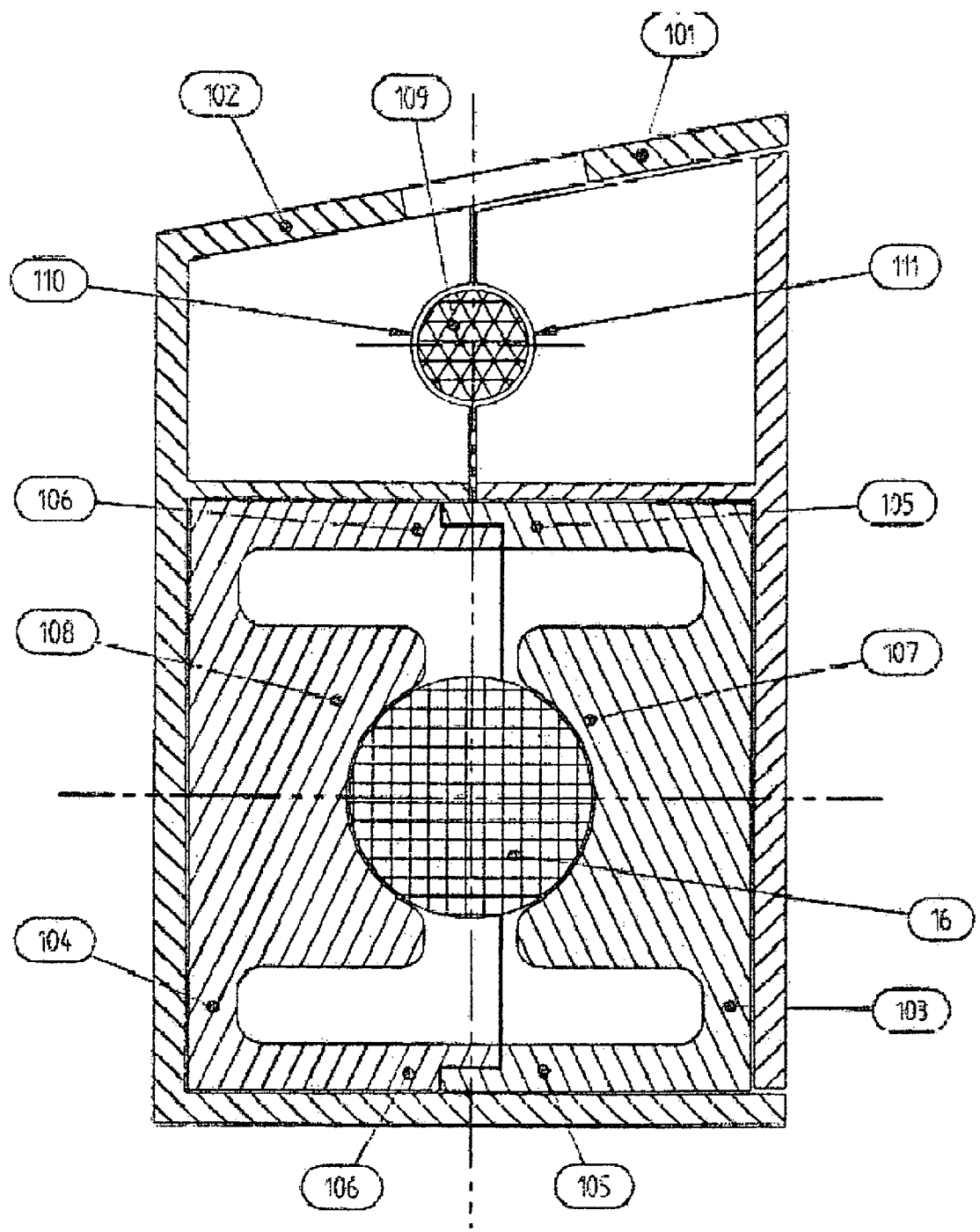

FIG. 4 shows a preferred form of the arrangement of the air pump 16 (for instance compressor) in the inhalation device. According to this preferred arrangement, the two-part housing 101, 102 of the inhalation device has bowl-like supports 103, 104 at the respective inner surfaces, the supports in assembled condition of the housing parts holding or supporting the air pump. The bowl-like supports 103, 104 preferably consist of a damping material, e.g., a corresponding cured damping foam so that the air pump is supported directly by the damping material. This reduces assembly costs since no separate supports need to be provided connecting the air pump to the housing for support. Further, it enables an easy exchange of the compressor. Only the two housing parts have to be disassembled and the compressor is then directly accessible and readily removable; possible supports do not have to be released before. Thus, the sound insulation means also serves as support.

The two bowl-like supports are preferably formed in the respective margin areas 105, 106 such that in the assembled state the edges overlap to obtain a better sealing.

Further, as shown in FIG. 4, the bowl-like supports preferably have corresponding projections 107, 108 extending into the interior of the housing in order to support the compressor. Thus, the projections 107, 108 are adapted in their outer form to the shape of the compressor.

Reference sign 109 relates to a connector which is held or attached in the two semicircular housing recesses 110, 111.

The invention claimed is:
1. An inhalation device comprising
a control;
an air pump; and
a downstream nebulizer, the air pump connected to the downstream nebulizer and connected to the control, wherein the control controls the air pump by voltage, or pulse-width modulation or both, such that it supplies an inhalation flow, or an inhalation volume or both, according to a predetermined time course to the nebulizer.

2. The inhalation device according to claim 1 further comprising a mouthpiece associated with the nebulizer.

3. The inhalation device according to claim 1 wherein the control of the air pump is carried out via the control depending on patient-individual lung function parameters.

4. The inhalation device according to claim 3 wherein the patient-individual lung function parameters are inhalation flow, or inhalation volume or both.

5. The inhalation device according to claim 3 wherein the control evaluates, on the basis of the patient-individual lung function parameters, the control voltage for the air pump which is necessary for obtaining a constant inhalation flow $Q_{target}$ individually determined for the patient.

6. The inhalation device according to claim 1 wherein the control performs a correction of the control voltage, or the pulse-width modulation or both when a measured actual inhalation flow $Q_{measurement}$ differs from a predetermined inhalation flow $Q_{target}$.

7. The inhalation device according to claim 6 wherein a flow-voltage characteristic is used dependent on the predetermined inhalation flow $Q_{target}$ and the measured actual inhalation flow $Q_{measurement}$ for a correction of the control voltage of the air pump.

8. The inhalation device according to claim 7 wherein the flow-voltage characteristic is further dependent on a cycle number of the specific air pump.

9. The inhalation device according to claim 1 wherein the control considers a counter-pressure generated by the patient.

10. The inhalation device according to claim 8 wherein the flow-voltage characteristic of the air pump is at first individually measured and afterwards approximated mathematically.

11. The inhalation device according to claim 1 wherein the control comprises a control for the drive of the air pump, a processing unit and a memory.

12. The inhalation device according to claim 11 wherein data representing patient-individual lung function parameters is stored in the memory.

13. The inhalation device according to claim 1 further comprising a reader to read external data carriers.

14. The inhalation device according to claim 13 wherein the reader is a SmartCard device reader and the external data carrier is a SmartCard device on which data are stored representing the patient-individual lung function parameters.

15. The inhalation device according to claim 1 further comprising a display unit and an input unit.

16. The inhalation device according to claim 1 further comprising a safety valve arranged downstream from the air pump.

17. The inhalation device according to claim 1 further comprising a pressure sensor arranged downstream from the air pump.

18. The inhalation device, according to claim 1 comprising an air pump and a pressure sensor for recognising the start of an inhalation process, wherein any or all of a pharmaceutical to be inhaled, an inhalation flow, or an inhalation volume can be individually set by the user, and wherein upon recognition of a first inhalation process by the pressure sensor, the individual parameters are set and the air pump is activated.

19. The inhalation device according to claim 18 wherein after the first inhalation or an inhalation stop, the user may optionally continue with the previous parameters or perform a reset of the parameters.

20. The inhalation device according to claim 1 wherein the air pump is a compressor or turbine.

21. The inhalation device according to claim 1 wherein an inhalation flow, or an inhalation volume or both, are kept basically constant during the predetermined time course.

22. The inhalation device according to claim 1 wherein an inhalation flow, or an inhalation volume or both, assume different levels during the predetermined time course.

23. The inhalation device according to claim 22 wherein the inhalation flow or the inhalation volume or both are kept basically constant.

24. A method for regulating an inhalation flow provided by an inhalation device according to claim 1 to a basically constant value by controlling the control voltage of the air pump of the inhalation device.

25. The method according to claim 24 wherein the control of the air pump takes place depending on patient-individual lung function parameters.

26. The method according to claim 25 wherein the patient-individual lung function parameters are inhalation flow, or inhalation volume or both.

27. The method according to claim 25 wherein on a basis of the patient-individual lung function parameters the control voltage for the air pump is determined to obtain a constant inhalation flow $Q_{target}$ individually predetermined for the patient.

28. The method according to claim 27 wherein a correction of the control voltage is performed when a measured actual inhalation flow $Q_{measurement}$ differs from the predetermined inhalation flow $Q_{target}$.

29. The method according to claim 28 wherein a flow-voltage characteristic depending on the predetermined inhalation flow $Q_{target}$ and the measured actual inhalation flow $Q_{measurement}$ is used to correct the control voltage of the air pump.

30. The method according to claim 29 wherein the flow-voltage characteristic of the air pump is at first individually determined by measurements and afterwards approximated mathematically.

* * * * *